United States Patent
Haddon (10) Patent No.: US 9,915,511 B1
(45) Date of Patent: Mar. 13, 2018

(54) UNPOWERED RAILGUN FIELD VALIDATION FOR SAFE-ARM FUZING

(71) Applicant: The United States of America as Represented by the Secretary of the Navy, Washington, DC (US)

(72) Inventor: Michael D. Haddon, Ridgecrest, CA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 194 days.

(21) Appl. No.: 15/089,686

(22) Filed: Apr. 4, 2016

(51) Int. Cl.
 *G01N 27/82* (2006.01)
 *F42C 21/00* (2006.01)
 *G01N 27/90* (2006.01)
 *G01N 27/83* (2006.01)

(52) U.S. Cl.
 CPC ............ *F42C 21/00* (2013.01); *G01N 27/82* (2013.01); *G01N 27/83* (2013.01); *G01N 27/90* (2013.01); *G01N 27/9013* (2013.01); *G01N 27/9026* (2013.01)

(58) Field of Classification Search
 CPC ........ G01N 27/82; G01N 27/83; G01N 27/90; G01N 27/9013; G01N 27/9026; G01N 27/9033; G01N 27/904
 USPC ... 324/51, 55, 200, 217, 219, 228, 233, 234, 324/239, 240, 257, 260
 See application file for complete search history.

(56) References Cited

U.S. PATENT DOCUMENTS

| | | | | |
|---|---|---|---|---|
| 2002/0150140 | A1* | 10/2002 | Julicher ................. | G01K 1/024 374/120 |
| 2014/0306551 | A1* | 10/2014 | Jost ........................ | G01R 19/00 307/131 |
| 2017/0285577 | A1* | 10/2017 | Godat .................... | G04C 3/143 |

* cited by examiner

*Primary Examiner* — Jermele M Hollington
*Assistant Examiner* — Raul Rios Russo
(74) *Attorney, Agent, or Firm* — James M. Saunders (57) ABSTRACT

Embodiments are directed to unpowered railgun field validation for safe-arm fuzing. Embodiments use a wire coil having an induced electromotive force voltage. At least one positive duration circuit measures the positive portion of the induced voltage. At least one positive peak duration circuit measures the peak value of the positive portion of the induced voltage. At least one negative duration circuit measures the duration value of the negative portion of the induced voltage. At least one negative peak detector circuit measures the peak value of the negative portion of the induced voltage.

20 Claims, 8 Drawing Sheets

UNPOWERED RAILGUN FIELD VALIDATION FOR SAFE-ARM FUZING

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention generally relates to magnetic field validation for fuzes.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF EMBODIMENTS OF THE INVENTION

Embodiments of the invention allow for the validation of the magnetic field environment for railgun munition safe-arm fuzing. It is the fuze's job to verify the proper environments and arm the weapon, or to reject an improper environment and safe the weapon. The magnetic field is unique and can be measured inside the munition to determine whether the munition has been fired from a gun.

The primary technical challenge with railgun munition fuzing is that power is not applied to the electronics before launch. This means that proving that a munition has been fired from a gun becomes difficult. Fortunately, the magnetic field generated is strong enough to penetrate the notional munition making the field suitable for validation as an arming environment.

Although embodiments of the invention are described in considerable detail, including references to certain versions thereof, other versions are possible. Examples of other versions include orienting the electrical components in alternating fashion. Therefore, the spirit and scope of the appended claims should not be limited to the description of versions included herein.

Conventions, Parameters, and Terminology

At the outset, it is helpful to describe various conventions, parameters, and terminology associated with embodiments of the invention.

Railgun: A railgun is sometimes referred to as a hyper velocity munition gun. The word "gun" herein is used to refer to "railgun."

Electro Motive Force (EMF): The electro motive force (EMF) is also sometimes referred to as the electromotive voltage (EMV) or induced electromotive force or voltage, or simply as the induced voltage.

Test Point: The term test point is sometimes abbreviated as TP and refers to locations where voltages are measured.

Nodes: Nodes are junctions of electrical connections and are shown on the associated figures as dots depicting the intersections of electrical connections. Additionally, some nodes are labeled such as, for example, "a," "A," "B," and the like to also indicate voltage measurement locations within the particular referenced circuit.

Theory of Operation: Embodiments of the invention use energy harvesting techniques and analog signal processing to store the duration and magnitude of the magnetic field by capturing the wave shape of the induced electro motive force (EMF), which is also known as an induced voltage and sometimes abbreviated as EMV for electromotive voltage. When power is applied to the fuze post-launch, the stored values indicating duration and magnitude can be used to determine whether the magnetic field values have the expected characteristics of being fired from a railgun. The expected characteristics describe the expected magnetic field profile of a railgun and munition. The expected characteristics can be based on modeled conditions associated with a specific railgun and munition. Likewise, the expected characteristics can also be from historical data from previous operations and testing in lookup tables, electronic libraries, and databases, each of which can be stored in the electronic memory of a computer such as, for example, an electronic processor associated with embodiments of the invention.

When the safe-arm fuze is powered, the voltages on the capacitors are read. The decision is then made if the magnetic field profile (positive and negative magnitude and durations of the induced EMF) are within an acceptable range. If either the duration or the magnitude voltages are incorrect, the fuze enters a safe "abort" mode.

Embodiments of the invention use a method of capturing the electromotive force (EMF), also known as the induced voltage, from the magnetic field by using Faraday's Law. Faraday's law is shown in Equation 1:

$$\varepsilon = -N\frac{(d\phi_B)}{dt}. \quad (1)$$

In Equation (1), $\varepsilon$ is the EMF produced, N is the number of turns in the coil, $\Phi_B$ is the magnetic flux, and t is the time. It is apparent from Equation (1) that EMF is proportional to the magnetic flux rate of change with respect to time. Capitalizing on the change in flux, power can now be harnessed for arming environment wave shape measurements.

Figure 2:
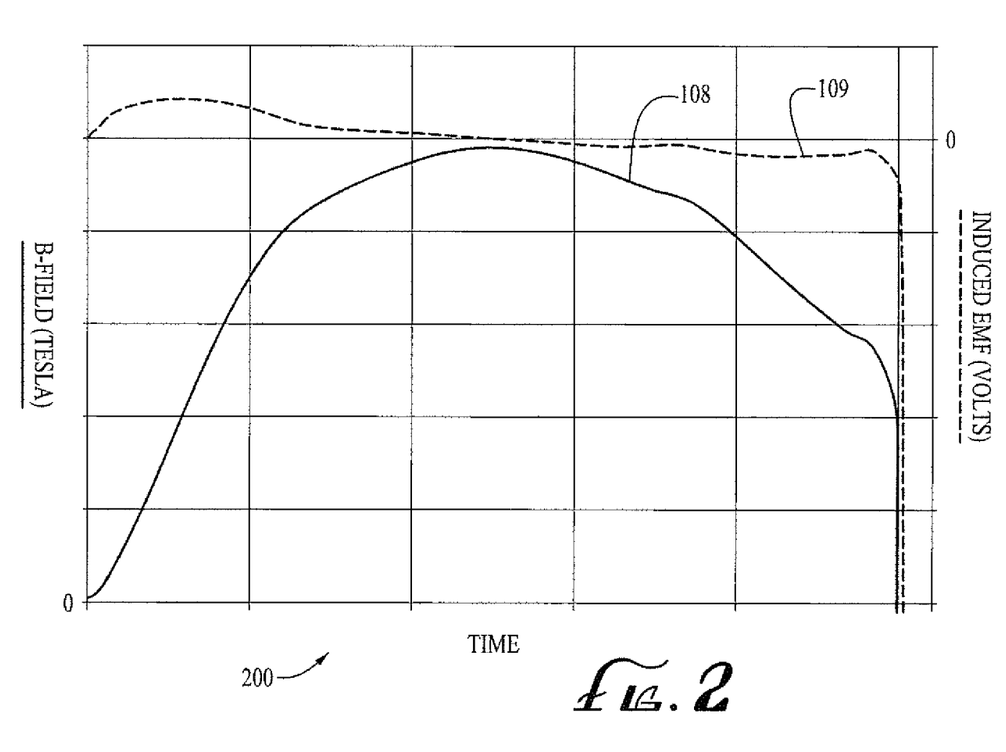
FIG. 2 is an illustration of a notional magnetic field and induced voltage versus time.

FIG. 2 illustrates a notional magnetic field 108 and induced voltage 109 versus time (time is depicted on the x-axis). FIG. 2 shows (with the polarity of the coil reversed to negate the minus sign in Faraday's law) that that an increasing magnetic field results in a positive voltage and a decreasing field results in a negative voltage.

Apparatus Embodiments

Figure 3:
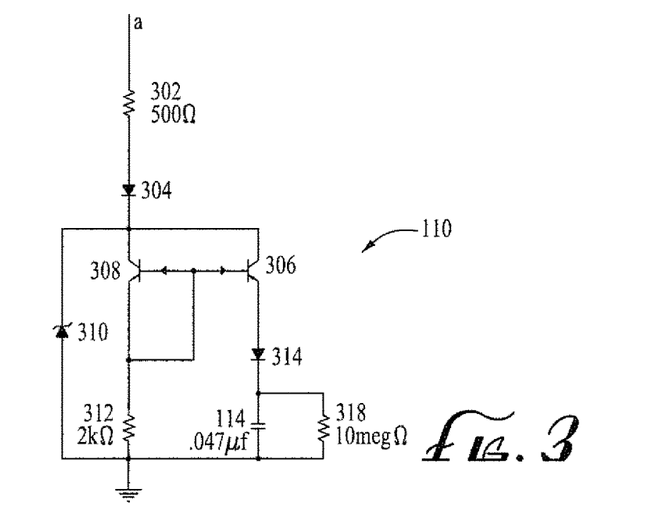
FIG. 3 is exemplary circuit diagram of a positive duration circuit (first circuit) used to validate the magnetic field environment, according to some embodiments of the invention.
Figure 5:
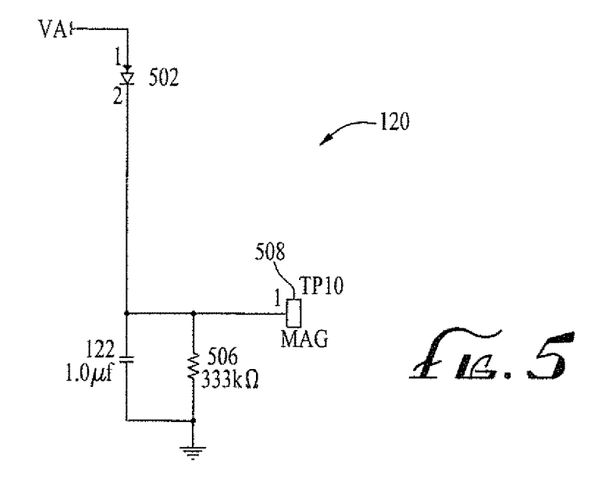
FIG. 5 is an exemplary circuit diagram of a positive peak detector circuit (second circuit) used to validate the magnetic field environment, according to some embodiments of the invention.
Figure 7:
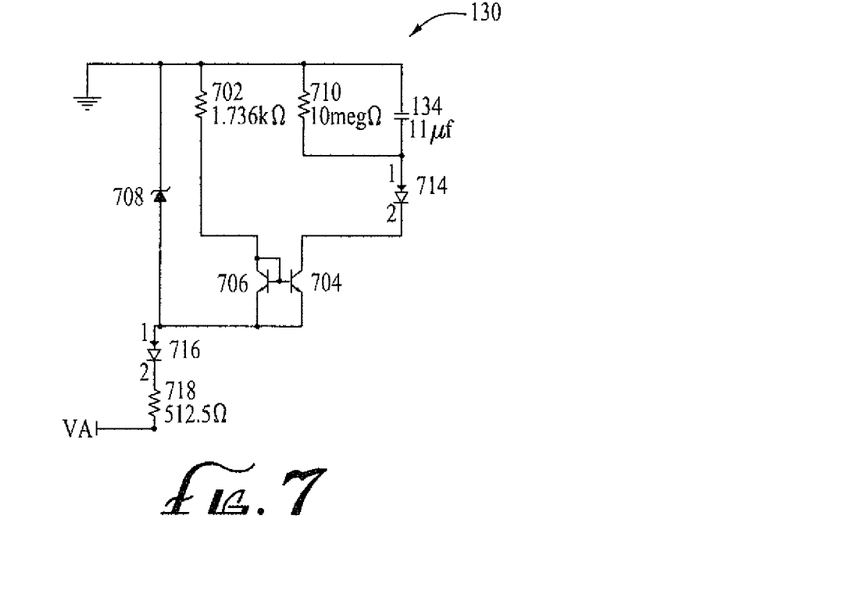
FIG. 7 is an exemplary circuit diagram of a negative duration circuit (third circuit) used to validate the magnetic field environment, according to some embodiments of the invention.
Figure 9:
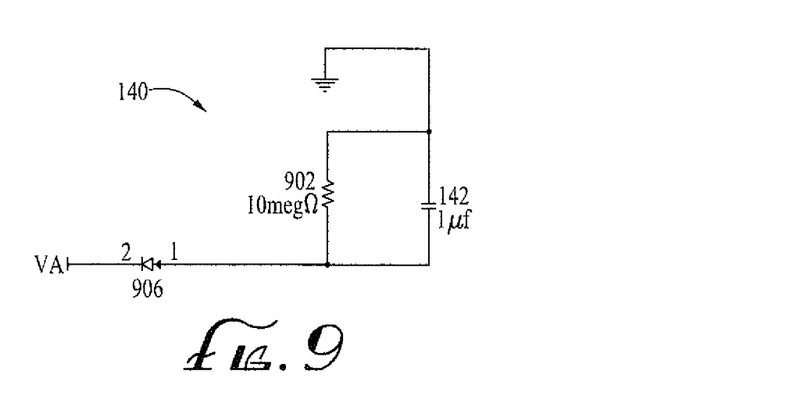
FIG. 9 is an exemplary circuit diagram of a negative peak detector circuit (fourth circuit) used to validate the magnetic field environment, according to some embodiments of the invention.
Figure 11:
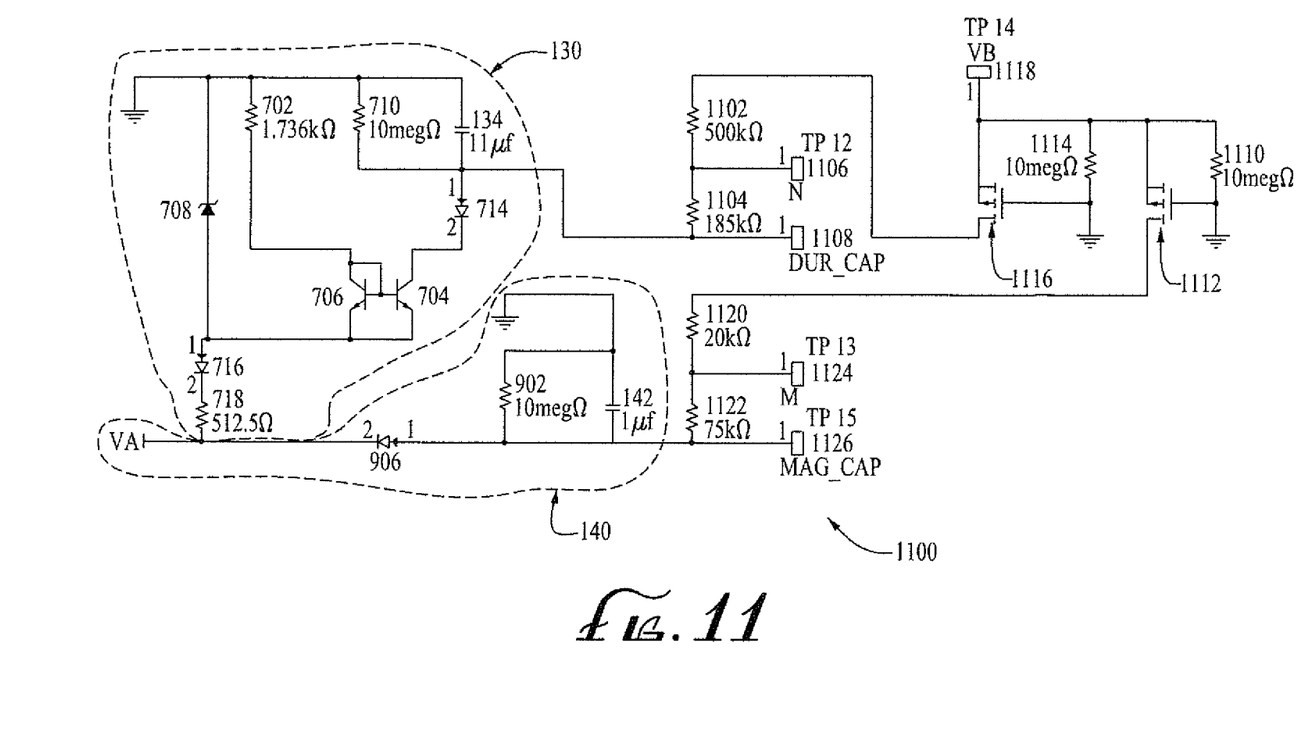
FIG. 11 illustrates additional circuitry that can be used to level shift voltages, according to some embodiments of the invention.

Embodiments of the invention use a plurality of circuits to validate the magnetic field environment. FIGS. 3, 5, 7, & 9 depict four exemplary circuits used to validate the magnetic field environment. FIG. 3 is exemplary circuit diagram of a positive duration circuit (sometimes referred to as the "first circuit") used to validate the magnetic field environment. FIG. 5 is an exemplary circuit diagram of a positive peak detector circuit (sometimes referred to as the "second circuit") used to validate the magnetic field environment. FIG. 7 is an exemplary circuit diagram of a negative duration circuit (sometimes referred to as the "third circuit") used to validate the magnetic field environment. FIG. 9 is an exemplary circuit diagram of a negative peak detector circuit (sometimes referred to as the "fourth circuit") used to validate the magnetic field environment. Additionally, FIG. 11 depicts an exemplary circuitry diagram that can be used to level shift voltages, if desired.

In embodiments, the purpose of the shown circuits is to capture the information of the wave-shape of the magnetic field profile. The values of the components (capacitors, resistors, diodes, and zener diodes) are optimized for the voltages, durations, and profile of the induced EMF. The magnetic field profile and induced EMF are notional.

Significant modeling indicated that other methods of constant current sources are viable with embodiments of the invention. These included constant current diodes, linear regulators configured as current sources, and current source chips. Additionally, a person having ordinary skill in the art will recognize that the depicted current mirrors yield constant current circuits, which are sometimes referred to as constant charge circuits.

Figure 1:
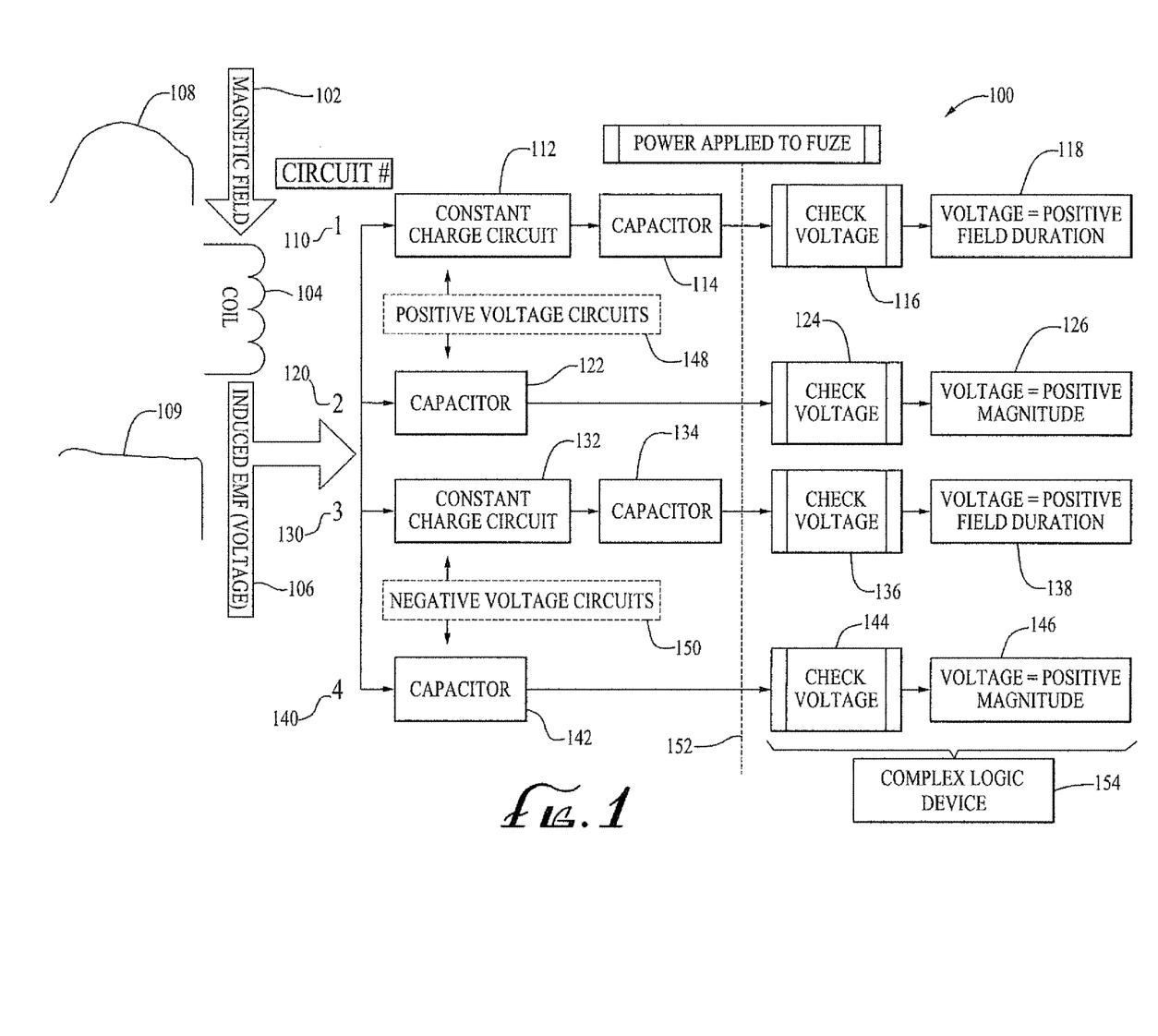
FIG. 1 is an exemplary operational environment for validating an unpowered safe-arm fuze, according to some embodiments of the invention.

FIG. 1 illustrates an exemplary operational environment, according to some embodiments of the invention, depicted as reference character 100. FIG. 1 also illustrates a system or tool for magnetic field validation in fuzes, and is also depicted with reference character 100. The method includes providing a munition. Munition examples include, but are not limited to, munitions out of cannons and guns. The munition is launched, which generates a magnetic field and EMF. The magnetic field and EMF are applied from the launched munition to the respective electronic circuits as a constant current.

A person having ordinary skill in the art will recognize that munitions (weapons) use thermal batteries to activate their associated fuzes. In the electronic circuits 110, 120, 130, & 140, the the munition's (weapon's) thermal battery is activated which causes the safe-arm fuze to come out of reset and begin checking the magnetic field conditions. The safe-arm fuze is powered and the particular voltages checked.

A wire coil 104 is used which has an associated magnetic field 102. The wire coil 104 has a first end and a second end. The wire coil 104 has an induced EMF (voltage) 106. The induced EMF (voltage) 106 has both positive and negative components. Two sets of circuits are used to measure both positive and negative duration and peak.

Embodiments combine a magnetic field 102 associated with the wire coil 104, the induced EMF (voltage) 106, energy harvesting, and analog processing to determine voltages in the associated circuitry. The energy harvesting is the process of using the induced EMF 106 to validate the circuitry. Analog processing is associated with the tasks after power is applied to a fuze (tasks to the right of the dashed line depicted as reference character 152). Reference character 108 is a small graphical illustration of the magnetic field generically shown by the first arrow (reference character 102). Likewise, reference character 109 is a small graphical illustration of the induced EMF (induced voltage) generically shown by the second arrow (reference character 106). Positive and negative voltage circuits are used.

Embodiments use a plurality of electrical circuits, as discussed below. Reference is made to at least four circuits. In particular, the terms first, second, third, and fourth electronic circuits are used and coincide with reference characters 110, 120, 130, and 140. As such, the first and second electronic circuits 110 & 120 are sometimes referred to as positive voltage circuits (designated by reference character 148). In general, the first and second electronic circuits 110 & 120 are used to measure the duration and peak values, respectively, of the positive portion of the induced voltage. The third and fourth circuits are used to measure the duration and peak values, respectively, of the negative portion of the induced voltage. Thus, the third and fourth electronic circuits 130 & 140 are sometimes referred to as negative voltage circuits (depicted by reference character 150). Embodiments of the invention can also include integrated circuits. When integrated circuits are used, a transient voltage suppressor is included to provide protection for the integrated circuits.

First Electronic Circuit

Referring to FIGS. 1 and 3, a first electronic circuit 110 is electrically-connected with the wire coil 104. The first electronic circuit 110 is a positive duration circuit configured to measure the duration value of the positive portion of the induced voltage. As shown in FIG. 1 with reference character 112, the first electronic circuit 110 is a constant charge circuit.

FIG. 3 illustrates the first electronic circuit. The first electronic circuit 110 includes a first positive duration resistor 302 electrically-connected in series to a first positive duration diode 304. A positive duration current mirror 306 & 308 is electrically-connected in series to the first positive duration diode. A positive duration zener diode 310 is electrically-connected in parallel with the positive duration current mirror. The positive duration zener diode is configured to maintain a 5 V DC current source to the positive duration current mirror 306 & 308.

A second positive duration resistor 312 is electrically-connected in series to the positive duration current mirror. A second positive duration diode 314 is electrically-connected in parallel with the positive duration current mirror. A positive duration capacitor 114 is electrically-connected in series to the second positive duration diode. The positive duration capacitor 114 is electrically-connected in parallel with the second positive duration resistor 318. The second positive duration resistor 312 is configured to provide a fixed current to the positive duration capacitor 114. A third positive duration resistor 318 is electrically-connected in parallel with the positive duration capacitor 114.

The first positive duration resistor 302 is about 500 ohms. The second positive duration resistor 312 is about 2 kilohms. The third positive duration resistor 318 is about 10 megaohms. The positive duration capacitor 114 is about 0.047 microfarads.

When charging a capacitor with constant current, the voltage becomes proportional to time. By constructing a circuit that charges with a constant current, it is possible to determine how long the input voltage has been over the circuit activation threshold. This is show mathematically in Equation 2:

$$dV = I\frac{dt}{C}. \quad (2)$$

Figure 4:
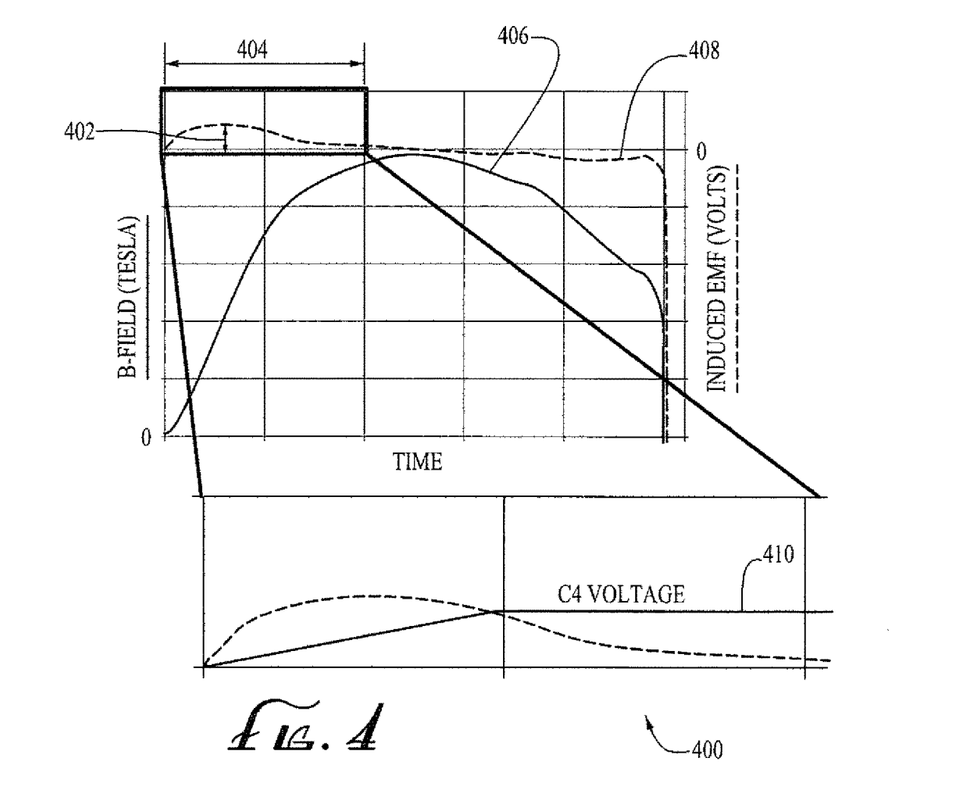
FIG. 4 is an exemplary graph depicting the positive duration associated with the positive duration circuit of FIG. 3, according to some embodiments of the invention.

The first electronic circuit 110 depicted in FIG. 3 uses the current mirror 306 & 308 with the current adjusted by the second positive duration resistor 312 to supply a fixed current to the positive duration capacitor 114 when the input voltage at "a" exceeds about 5 V DC. The positive duration zener diode 310 maintains about a 5 V DC source to the positive duration current mirror 306 & 308 to maintain linearity. This allows the voltage on the positive duration capacitor 114 to become roughly (about) equivalent to the time the input voltage "a" exceeds 5 V DC. In FIG. 4, the magnetic field and the induced EMF voltage experienced by the positive duration capacitor 114 is shown with reference characters 406 and 408, respectively. In the exploded view of FIG. 4, reference characters 402 and 404 are the positive peak and positive duration, respectively, for the positive duration capacitor 114. Stated another way, FIG. 4 may also be thought of as measuring the duration of the positive EMF pulse.

The positive duration capacitor 114 is sometimes denoted as "C4" for a simple reference. Thus, when a reference is made to "C4," the designation refers to the positive duration capacitor 114 associated with the first electronic circuit 110, as depicted in FIGS. 1 & 3. In the exploded view of FIG. 4, the induced EMF 408 experiences a positive slope in the first region of the exploded view (the left-hand panel of the exploded view). The duration being measured associated with the positive duration capacitor 114 is the duration coinciding with the positive slope of the induced EMF 408, which is in the first region (the left-hand panel of the exploded view). The slope of the induced EMF 408 is depicted with reference character 410. The slope 410 of the induced EMF 408 is then flat in the second region (the right-hand panel of the exploded view).

Second Electronic Circuit

Figure 6:
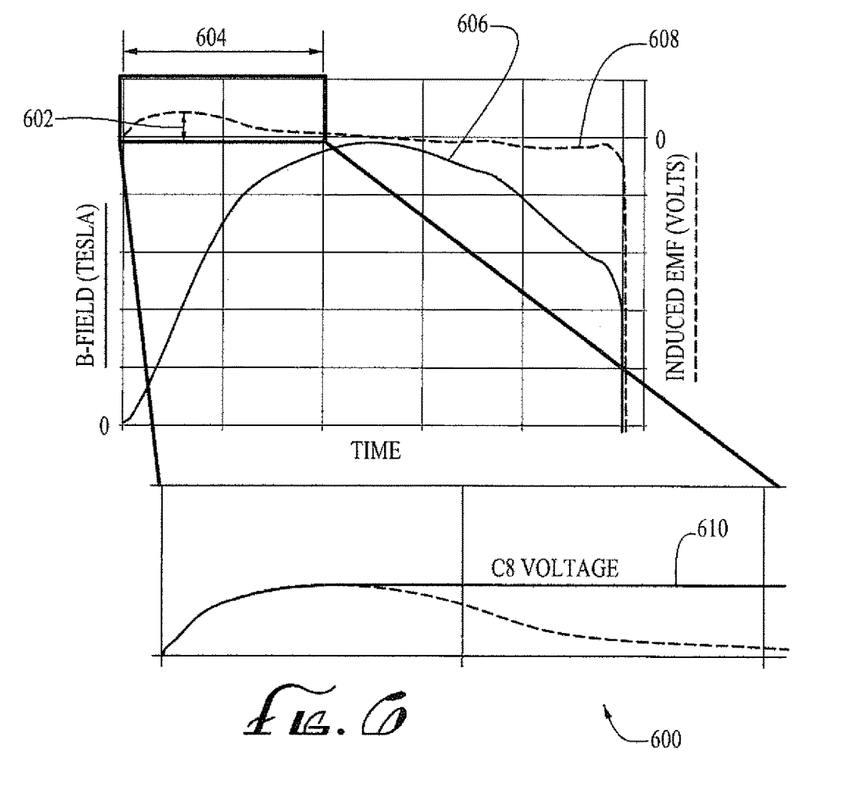
FIG. 6 is an exemplary graph depicting the positive peak associated with the positive peak detector circuit of FIG. 5, according to some embodiments of the invention.

Referring to FIGS. 1 and 5, a second electronic circuit 120 is electrically-connected to the wire coil 104. The second electronic circuit 120 is a positive peak duration circuit configured to measure the peak value of the positive portion of the induced voltage. The second electronic circuit includes a positive peak duration diode 502 electrically-connected in series to a positive peak detector capacitor 122. A positive peak detector resistor 506 is electrically-connected in parallel with the positive peak detector capacitor 122. The positive peak detector capacitor 122 is about 1 microfarads and the positive peak detector resistor 506 is about 333 kiliohms. In FIG. 6, the magnetic field and the induced EMF voltage experienced by the positive peak detector capacitor 122 is shown with reference characters 606 and 608, respectively. In the exploded view of FIG. 6, reference characters 602 and 604 are the positive peak and positive duration, respectively, for the positive peak detector capacitor 122.

The positive peak detector capacitor 122 is sometimes denoted as "C8" for a simple reference. Thus, when a reference is made to "C8," the designation refers to the positive peak detector capacitor 122 associated with the second electronic circuit 120, as depicted in FIGS. 1 & 5. In the exploded view of FIG. 6, the induced EMF 608 experiences a positive induced voltage in the first region of the exploded view (the left-hand panel of the exploded view). Conversely, the induced EMF 608 experiences a negative induced voltage in the second region (the right-hand panel of the exploded view). The positive peak voltage 602 measurement occurs in the first region. Reference character 610 depicts the measured peak positive peak voltage 602 from the positive peak detector capacitor 122.

Third Electronic Circuit

Referring to FIGS. 1 and 7, a third electronic circuit 130 is electrically-connected with the wire coil 104. The third electronic circuit 130 is a negative duration circuit configured to measure the duration value of the negative portion of the induced voltage. As shown in FIG. 1 with reference character 132, the third electronic circuit 130 is a constant charge circuit.

The third electronic circuit 130 includes a first negative duration resistor 702 electrically-connected in series to a negative duration current mirror 704 & 706. A negative duration zener diode 708 is electrically-connected in parallel with the first negative duration resistor 702. The negative duration zener diode is configured to maintain a 5V DC current source to the negative duration current mirror 704 & 706. A second negative duration resistor 710 is electrically-connected in parallel with the first negative duration resistor 702. A negative duration capacitor 134 is electrically-connected in parallel with the second negative duration resistor 710. The first negative duration resistor 702 is configured to supply a fixed current to the negative duration capacitor 134. A first negative duration diode 714 has a first end and a second end. The first end of the negative duration diode 714 is electrically-connected in series to the parallel connection of the negative duration capacitor 134 and the second negative duration resistor 710. The second end of the negative duration diode 714 is electrically-connected in series with the negative duration current mirror 704 & 706. The negative duration current mirror 704 & 706 has an output electrically-connected to a second negative duration diode 716. The second negative duration diode 716 is electrically connected in series to a third negative duration resistor 718. The first negative duration resistor 702 is about 1736 ohms. The second negative duration resistor 710 is about 10 megaohms. The third negative duration resistor 718 is about 512 ohms. The negative duration capacitor 134 is about 11 microfarads.

The third electronic circuit 130 can be analyzed using Equation 2 above. As shown in FIG. 7, the third electronic circuit 130 uses the current mirror 704 & 706, with the current adjusted by the first negative duration resistor 702 to supply a fixed current to the negative duration capacitor 134 when the input voltage at $V_A$ exceeds about 5 V DC. The zener diode 708 maintains about a 5 V DC to the current mirror 704 & 706 to maintain linearity. This allows the voltage on the negative duration capacitor 134 to become roughly (about) equivalent to the time the input voltage exceeds about −5 V DC.

Figure 8:
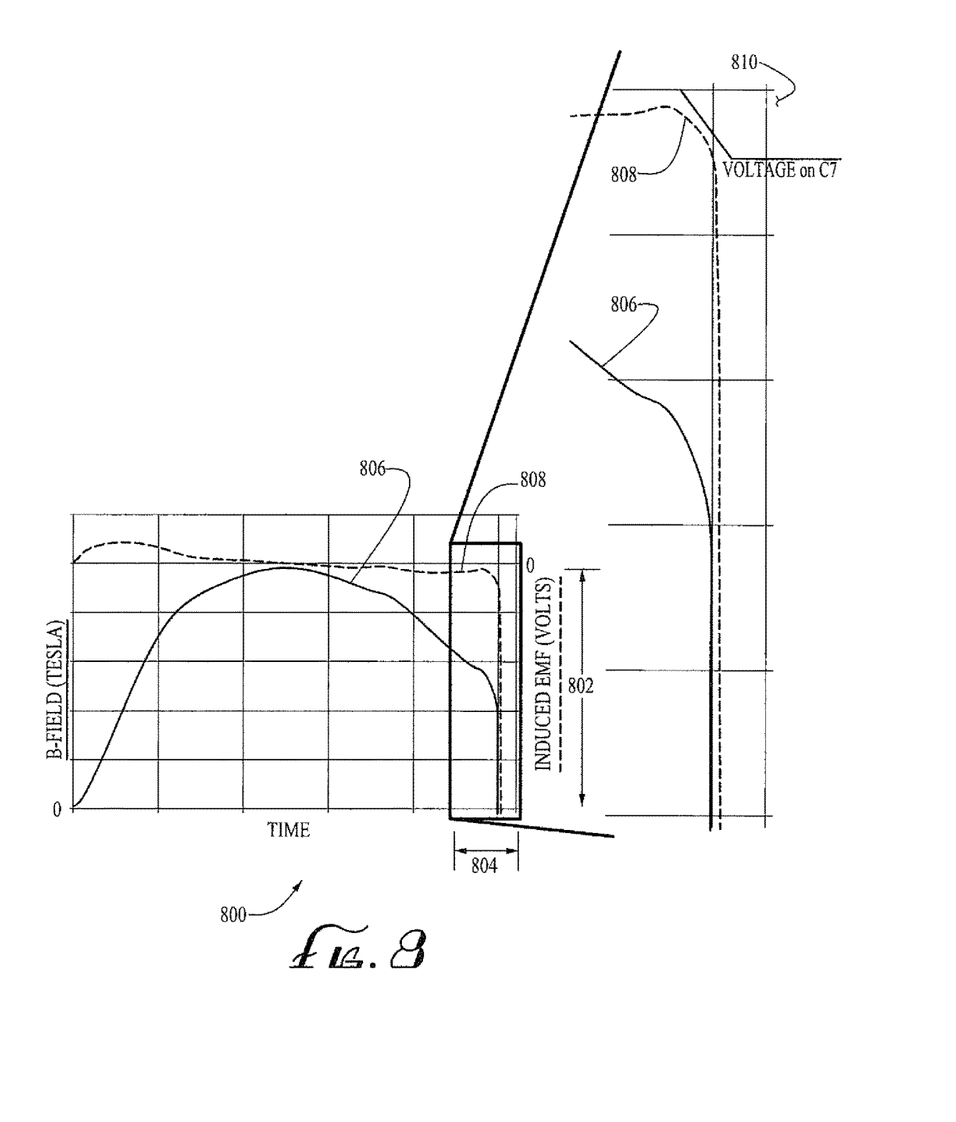
FIG. 8 is an exemplary graph depicting the negative duration associated with the negative duration circuit of FIG. 7, according to some embodiments of the invention.

In FIG. 8, the magnetic field and the induced EMF voltage experienced by the negative duration capacitor 134 is shown with reference characters 806 and 808, respectively. In the exploded view of FIG. 8, reference characters 802 and 804 are the negative peak and negative duration, respectively, for the negative duration capacitor 134.

The negative duration capacitor 134 is sometimes denoted as "C7" for a simple reference. Thus, when a reference is made to "C7," the designation refers to the negative duration capacitor 134 associated with the third electronic circuit 130, as depicted in FIGS. 1 & 7. In the exploded view of FIG. 8, the induced EMF 808 experiences a negative slope (near the upper portion of the exploded view) and is driven down into the negative voltage ranges (through the bottommost panels of the exploded view). The duration being measured associated with the negative duration capacitor 134 is the duration coinciding with the negative slope of the induced EMF 808, which coincides with the span beneath the horizontal line labeled "VOLTAGE on C7." Reference character 810 is very close to (about) the negative slope of the induced EMF 808. Stated another way, FIG. 8 may also be thought of as measuring the duration of the negative EMF pulse.

Fourth Electronic Circuit

Referring to FIGS. 1 and 9, a fourth electronic circuit 140 is electrically-connected with the wire coil 104. The fourth electronic circuit 140 is a negative duration circuit configured to measure the peak value of the negative portion of the induced voltage.

The fourth electronic circuit 140 includes a negative peak detector resistor 902 electrically-connected in parallel with a negative peak detector capacitor 142. A negative peak detector diode 906 is electrically-connected in series to the parallel connection of the negative peak detector resistor 902 and the negative peak detector capacitor 142. The negative peak detector resistor 902 is about 10 megaohms and the negative peak detector capacitor 142 is about 1 microfarad.

Figure 10:
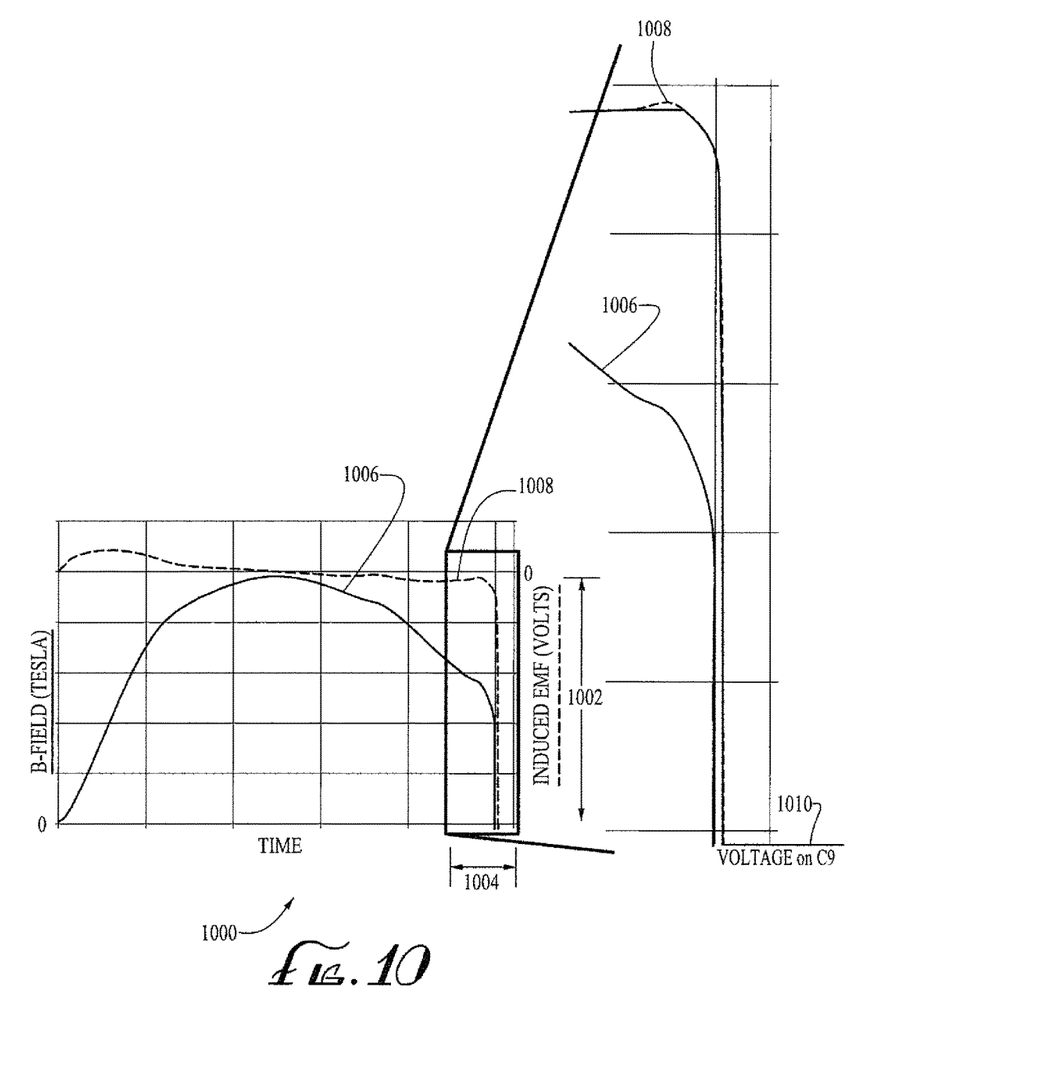
FIG. 10 is an exemplary graph depicting the negative peak associated with the negative peak detector circuit of FIG. 9, according to some embodiments of the invention.

In FIG. 10, the magnetic field and the induced EMF voltage experienced by the negative peak detector capacitor 142 is shown with reference characters 1006 and 1008, respectively. In the exploded view of FIG. 10, reference characters 1002 and 1004 are the negative peak and negative duration, respectively, for the negative peak detector capacitor 142.

The negative peak detector capacitor 142 is sometimes denoted as "C9" for a simple reference. Thus, when a reference is made to "C9," the designation refers to the negative peak detector capacitor 142 associated with the third electronic circuit 140, as depicted in FIGS. 1 & 8. In the exploded view of FIG. 10, the induced EMF 1008 experiences a negative induced voltage through the bottommost panel in the exploded view. The negative peak voltage measurement occurs in the bottom-most region and is referenced as the "VOLTAGE on C9" with reference character 1010.

A complex logic device 154 is electrically-connected to each of the first electronic circuit 110, the second electronic circuit 120, the third electronic circuit 130, and the fourth electronic circuit 140. It is understood that the electrical connection of the complex logic device 154 with the first, second, third, and fourth electronic circuits 110, 120, 130, & 140 includes communication connections, including wireless connections. The complex logic device 154, in some embodiments, is a microcontroller and is embodied in the tasks shown to the right of the dashed line 152. In other embodiments, the complex logic device 154 is a field programmable gate array (FPGA). While in other embodiments, the complex logic device 154 is a complex programmable logic device (CPLD) such as, for example, a programmable logic device. The complex logic device 154 is configured to measure voltages in each of the first, second, third, and fourth electronic circuits.

Additional circuitry can be used to level shift the voltages so that they can be measured by an analog-to-digital converter that works with positive input voltages. For instance, FIG. 11 illustrates additional circuitry used to convert negative voltages to positive voltages at the time the fuze is turned on. Reference character 1100 is used to depict the combination of the third and fourth electronic circuits 130 & 140 and the additional circuitry (depicted with even number reference characters 1102 through 1126). The third and fourth electronic circuits 130 & 140 are shown in conjunction with the additional circuitry (even number reference characters 1102 through 1126).

Due to the voltages on the negative duration capacitor 134 and the negative peak detector capacitor 142 being negative, the additional circuitry (even reference characters 1102 through 1126) can be added for level shifting. When node $V_B$ (reference character 1118 and also designated as "TP 14" for "test point 14") is 0 V DC, no current flows through first transistor 1116, and the negative duration capacitor 134 is unaffected by resistors 1104 and 1102. When 3.3 V DC is applied to $V_B$, just prior to measuring the voltage on the negative duration capacitor 134, the resistors 1104 and 1102 act as a voltage divider. When the negative duration capacitor 134 is charged to a correct range of voltages, the value at test point 12 (TP 12) (reference character 1106) becomes a positive voltage representing the negative duration capacitor's 134 voltage, as the voltage on $V_B$ is fixed at 3.3 V DC. The correct range of voltages from the voltage divider formed by resistors 1104 and 1102 is at the ratio needed to bring the voltage at TP 12 (reference character 1106) positive. As depicted, the additional circuitry in this portion of the circuit in FIG. 11 is configured to detect voltages as low as −1.4 V DC.

When node $V_B$ is 0 V DC, no current can flow through a second transistor 1112, and the negative peak detector capacitor 142 is unaffected by resistors 1122 and 1120. When 3.3 V DC is applied to $V_B$, just prior to measuring the voltage on the negative peak detector capacitor, resistors 1122 and 1120 act as a voltage divider. When the negative peak detector capacitor 142 is charged to a correct range of voltages, the value at test point (TP 13) (reference character 1124) becomes a positive voltage representing the voltage on the negative peak detector capacitor 142, as the voltage on $V_B$ is fixed at 3.3 V DC. The correct range of voltages from the voltage divider formed by resistors 1122 and 1120 is at the ratio needed to bring the voltage at TP 13 (reference character 1124) positive. As depicted, the additional circuitry in this portion of the circuit in FIG. 11 is configured to detect voltages as low as −11.7 V DC.

The additional circuitry in FIG. 11 includes pull-up resistors. The pull-up resistors are depicted with reference characters 1110 & 1114 and are each about 10 megaohms. The purpose for the pull-up resistors 1110 & 1114 are to keep the gates of the transistors 1112 & 1116 from floating and turning on.

The complex logic device (such as the microcontroller) 154 measures (sometimes referred to as "check") voltages in the first, second, third, and fourth electronic circuits 110, 120, 130, & 140. The checking of the checking of the voltages on the respective circuits is illustrated in the boxes shown by reference characters 116, 124, 136, & 144 in FIG. 1. The first electronic circuit's 110 voltage coincides with the positive field duration (reference character 118). The second electronic circuit's 120 voltage coincides with the positive magnitude (reference character 126). The third electronic circuit's 130 voltage coincides with the negative field duration (reference character 138). The fourth electronic circuit's 140 voltage coincides with the negative magnitude (reference character 146).

Some figures depict locations for the complex logic device 154 to measure voltages such as the test point locations (reference characters 508, 1106, 1108, 1118, 1124, and 1126). Additionally, some of the same test point locations depict abbreviations for magnitude and duration associated with the respective capacitors, especially "MAG" for reference character 508, "DUR_CAP" for reference character 1108, and "MAG_CAP" for reference character 1126. The complex logic device 154 compares the voltages measured against the values stored in lookup tables to validate the magnetic field environment. When the magnetic field environment is validated, the fuze progresses in the arming process.

The complex logic device 154 is instructed to determine whether the magnetic field profile is within an acceptable range. When either the duration or magnitude calculations are incorrect, the fuze is instructed to enter a safe mode. An "incorrect" state refers to when the measurements fall outside the acceptable ranges, causing the fuze to enter a safe mode. Thus, the calculations are considered "incorrect" when the voltages are determined to be less than about 1.65 V DC. The deduction is that measurements falling outside the acceptable ranges are the result of a munition that was not fired (such as a squib load) or a dropped munition.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the appended claims.

What is claimed is:

1. A magnetic field validation circuit for a safe-arm device, comprising:
    a wire coil having a first end and a second end, said wire coil having an induced EMF voltage;
    a first electronic circuit electrically-connected with said wire coil, said first electronic circuit is a positive duration circuit configured to measure the duration value of the positive portion of the induced voltage;
    a second electronic circuit electrically-connected with said wire coil, said second electronic circuit is a positive peak duration circuit configured to measure the peak value of the positive portion of the induced voltage;
    a third electronic circuit electrically-connected with said wire coil, said third electronic circuit is a negative duration circuit configured to measure the duration value of the negative portion of the induced voltage;
    a fourth electronic circuit electrically-connected with said wire coil, said fourth electronic circuit is a negative peak detector circuit configured to measure the peak value of the negative portion of the induced voltage; and
    a complex logic device electrically-connected to each of said first electronic circuit, said second electronic circuit, said third electronic circuit, and said fourth electronic circuit.

2. The magnetic field validation circuit according to claim 1, wherein said first electronic circuit, comprising:
    a first positive duration resistor electrically-connected in series to a first positive duration diode;
    a positive duration current mirror electrically-connected in series to said first positive duration diode;
    a positive duration zener diode electrically-connected in parallel with said positive duration current mirror, said positive duration zener diode configured to maintain a 5 V DC current source to said positive duration current mirror;
    a second positive duration resistor electrically-connected in series to said positive duration current mirror;
    a second positive duration diode electrically-connected in parallel with said positive duration current mirror;
    a positive duration capacitor electrically-connected in series to said second positive duration diode;
    wherein said positive duration capacitor is electrically-connected in parallel with said second positive duration resistor, said second positive duration resistor is configured to provide a fixed current to said positive duration capacitor; and
    a third positive duration resistor electrically-connected in parallel with said positive duration capacitor.

3. The magnetic field validation circuit according to claim 2, wherein said first positive duration resistor is about 500 ohms, said second positive duration resistor is about 2 kiliohms, said third positive duration resistor is about 10 megaohms, and said positive duration capacitor is about 0.047 microfarads.

4. The magnetic field validation circuit according to claim 1, wherein said second electronic circuit, comprising:
    a positive peak duration diode electrically-connected in series to a positive peak detector capacitor; and
    a positive peak detector resistor electrically-connected in parallel with said positive peak detector capacitor.

5. The magnetic field validation circuit according to claim 4, wherein said positive peak detector capacitor is about 1 microfarads and said positive peak detector resistor is about 333 kiliohms.

6. The magnetic field validation circuit according to claim 1, wherein said third electronic circuit, comprising:
    a first negative duration resistor electrically-connected in series to a negative duration current mirror;
    a negative duration zener diode electrically-connected in parallel with said first negative duration resistor, wherein said negative duration zener diode configured to maintain a 5V DC current source to said negative duration current mirror;
    a second negative duration resistor electrically-connected in parallel with said first negative duration resistor;
    a negative duration capacitor electrically-connected in parallel with said second negative duration resistor, said first negative duration resistor configured to supply a fixed current to said negative duration capacitor;
    a first negative duration diode having a first end and a second end, said first end electrically-connected in series to said parallel connection of said negative duration capacitor and said second negative duration resistor, wherein said second end electrically connected in series with said negative duration current mirror;

wherein said negative duration current mirror having an output electrically-connected to a second negative duration diode, said second negative duration diode electrically connected in series to a third negative duration resistor.

7. The magnetic field validation circuit according to claim 6, wherein said first negative duration resistor is about 1736 ohms, said second negative duration resistor is about 10 megaohms, said third negative duration resistor is about 512 ohms, and said negative duration capacitor is about 11 microfarads.

8. The magnetic field validation circuit according to claim 1, said fourth electronic circuit, comprising:
   a negative peak detector resistor electrically-connected in parallel with a negative peak detector capacitor; and
   a negative peak detector diode electrically-connected in series to said parallel connection of said negative peak detector resistor and said negative peak detector capacitor.

9. The magnetic field validation circuit according to claim 8, wherein said negative peak detector resistor is about 10 megaohms and said negative peak detector capacitor is about 1 microfarad.

10. The magnetic field validation circuit according to claim 1, wherein said complex logic device is configured to measure voltages in each of said first, second, third, and fourth electronic circuits.

11. A magnetic field validation tool for safe-arm fuzing, comprising:
   a wire coil having a first end and a second end, said wire coil having an induced EMF voltage;
   an analog processing system electrically-connected to said wire coil; and
   a complex logic device electrically-connected to said analog processing system.

12. The tool according to claim 11, said analog processing system, further comprising:
   a first electronic circuit electrically-connected with said wire coil, said first electronic circuit is a positive duration circuit configured to measure the duration value of the positive portion of the induced voltage;
   a second electronic circuit electrically-connected with said wire coil, said second electronic circuit is a positive peak duration circuit configured to measure the peak value of the positive portion of the induced voltage;
   a third electronic circuit electrically-connected with said wire coil, said third electronic circuit is a negative duration circuit configured to measure the duration value of the negative portion of the induced voltage;
   a fourth electronic circuit electrically-connected with said wire coil, said fourth electronic circuit is a negative peak detector circuit configured to measure the peak value of the negative portion of the induced voltage.

13. The tool according to claim 12, wherein said first electronic circuit, comprising:
   a first positive duration resistor electrically-connected in series to a first positive duration diode;
   a positive duration current mirror electrically-connected in series to said first positive duration diode;
   a positive duration zener diode electrically-connected in parallel with said positive duration current mirror, said positive duration zener diode configured to maintain a 5 V DC current source to said positive duration current mirror;
   a second positive duration resistor electrically-connected in series to said positive duration current mirror;
   a second positive duration diode electrically-connected in parallel with said positive duration current mirror;
   a positive duration capacitor electrically-connected in series to said second positive duration diode;
   wherein said positive duration capacitor is electrically-connected in parallel with said second positive duration resistor, said second positive duration resistor is configured to provide a fixed current to said positive duration capacitor; and
   a third positive duration resistor electrically-connected in parallel with said positive duration capacitor.

14. The tool according to claim 13, wherein said first positive duration resistor is about 500 ohms, said second positive duration resistor is about 2 kiliohms, said third positive duration resistor is about 10 megaohms, and said positive duration capacitor is about 0.047 microfarads.

15. The tool according to claim 12, wherein said second electronic circuit, comprising:
   a positive peak duration diode electrically-connected in series to a positive peak detector capacitor; and
   a positive peak detector resistor electrically-connected in parallel with said positive peak detector capacitor.

16. The tool according to claim 12, wherein said third electronic circuit, comprising:
   a first negative duration resistor electrically-connected in series to a negative duration current mirror;
   a negative duration zener diode electrically-connected in parallel with said first negative duration resistor, wherein said negative duration zener diode configured to maintain a 5V DC current source to said negative duration current mirror;
   a second negative duration resistor electrically-connected in parallel with said first negative duration resistor;
   a negative duration capacitor electrically-connected in parallel with said second negative duration resistor, said first negative duration resistor configured to supply a fixed current to said negative duration capacitor;
   a first negative duration diode having a first end and a second end, said first end electrically-connected in series to said parallel connection of said negative duration capacitor and said second negative duration resistor, wherein said second end electrically connected in series with said negative duration current mirror;
   wherein said negative duration current mirror having an output electrically-connected to a second negative duration diode, said second negative duration diode electrically connected in series to a third negative duration resistor.

17. The tool according to claim 16, wherein said first negative duration resistor is about 1736 ohms, said second negative duration resistor is about 10 megaohms, said third negative duration resistor is about 512 ohms, and said negative duration capacitor is about 11 microfarads.

18. The tool according to claim 16, said fourth electronic circuit, comprising:
   a negative peak detector resistor electrically-connected in parallel with a negative peak detector capacitor; and
   a negative peak detector diode electrically-connected in series to said parallel connection of said negative peak detector resistor and said negative peak detector capacitor.

19. The tool according to claim 18, wherein said negative peak detector resistor is about 10 megaohms and said negative peak detector capacitor is about 1 microfarad.

20. The tool according to claim 12, wherein said complex logic device is configured to measure voltages in each of said first, second, third, and fourth electronic circuits.

\* \* \* \* \*